United States Patent [19]

Grau et al.

[11] Patent Number: 4,850,966
[45] Date of Patent: Jul. 25, 1989

[54] DEVICE FOR THE ADMINISTRATION OF MEDICAMENT SUSPENSIONS

[75] Inventors: Ulrich Grau; Wolfgang Pohler, both of Hofheim am Taunus, Fed. Rep. of Germany

[73] Assignee: Hoechst Aktiengesellschaft, Frankfurt am Main, Fed. Rep. of Germany

[21] Appl. No.: 17,617

[22] Filed: Feb. 24, 1987

[30] Foreign Application Priority Data

Feb. 26, 1986 [DE] Fed. Rep. of Germany ....... 3606163

[51] Int. Cl.⁴ ............................................ A61M 37/00
[52] U.S. Cl. ...................................... 604/82; 604/903
[58] Field of Search ......................... 604/82, 218, 903

[56] References Cited

U.S. PATENT DOCUMENTS 3,734,079  5/1973  Weber ................................ 604/218
4,129,131 12/1978  Naftulin ............................. 604/903
4,135,510  1/1979  Assovly ............................. 604/218

FOREIGN PATENT DOCUMENTS 0058536 of 0000 European Pat. Off. .
0143895 of 0000 European Pat. Off. .
82/02622 2/1982 PCT Int'l Appl. .

Primary Examiner—John D. Yasko
Attorney, Agent, or Firm—Finnegan, Henderson, Farabow, Garrett, & Dunner

[57] ABSTRACT

A medicament container, such as an injection ampule, for multiple administration of medicament suspensions the containers is filled with medicament so as to be free of gas bubbles, and includes at least one inert mixing element of suitable size whose density is different from that of the suspension. The mixing element acts to homogenize the medicament suspension as the container is shaken.

11 Claims, 1 Drawing Sheet

U.S. Patent      Jul. 25, 1989      4,850,966
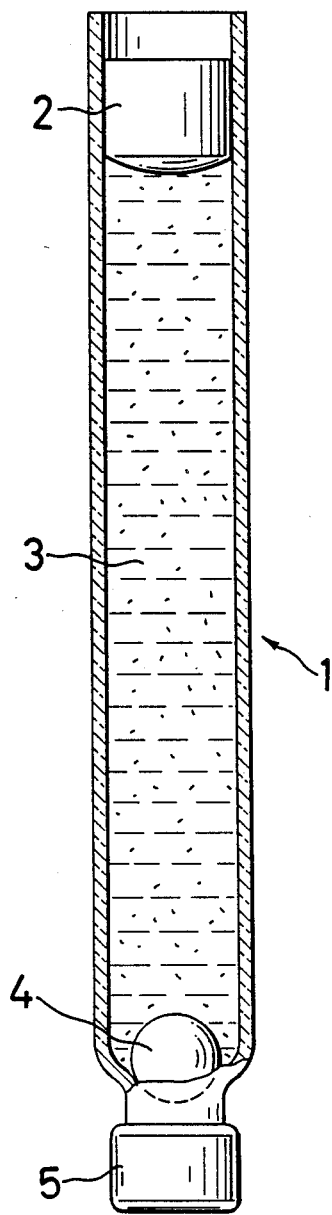

DEVICE FOR THE ADMINISTRATION OF MEDICAMENT SUSPENSIONS

BACKGROUND OF THE INVENTION

Portable infusion devices are known for automatic delivery of liquids, particularly insulin, these liquids being contained in replaceable injection ampules (European Patent Application No. 0,143,895, and the devices mentioned therein). Portable multidose injection devices, so-called "pens" (EP-A No. 0,058,536 and PCT Application WO No. 82/02,662) are furthermore known. However, these known devices, which are intended for multiple administration of the medicaments, are only suitable for homogeneous liquids, particularly solutions. In the case of disperse systems, such as medicament suspensions, the danger exists not only that crystal settling causes mechanical problems, but, above all, incorrect dosages are caused. Such incorrect dosages are particularly critical when the medicament is a highly-active medicament of narrow therapeutic range, such as, for example, insulin.

If, in the case of an insulin suspension, too few crystals are administered because the suspension has been inadequately shaken or has already settled again, hyperglycemia is to be expected, along with the known accompanying symptoms and with increased risk of later complications. If, in contrast, too much of the active ingredient is administered, hyperinsulinemia and hypoglycemia are to be feared, along with the accompanying serious symptoms, such as sweating, cramps and unconsciousness, up to death caused by hypoglycemic shock.

Medicament suspensions are usually filled into containers which also contain a gas space above the suspension. The suspension can then be homogenized by rolling, inverting or shaking this container. The presence of the gas bubble and its mobility is responsible for this. If, in contrast, the suspension is filled so that there is essentially no gas space, for example in cylindrical ampules from which multiple administrations are to take place, homogeneous mixing is normally not possible in a reasonable time. The physical basis of this phenomenon is that the density of crystals is generally very similar to the density of the medium.

In the case of dispensing devices in which multiple doses are to be administered from a stock, essentially gas bubble-free filling is necessary, however, since only then is reproduceable dose administraion ensured. "Essentially gas bubble-free" here is not intended to exclude a more or less large amount of gas being present initially, that is to say, for example, in the initial ampule, which is, however, removed in a known fashion before the first administration so that the liquid is then virtually free of gas bubbles. However, gas bubble-free crystal suspensions cannot be converted into the necessary homogeneous form by shaking in an acceptable period of time. It should particularly be taken into account here that such a homogenization must also be possible for old and handicapped patients.

SUMMARY OF THE INVENTION

It is an object of the present invention to provide storage containers which are suitable for infusion and injection devices and in which medicament suspensions can also be homogenized by shaking in the absence of a gas bubble.

This is complicated by the fact that the sterility of the contents necessary for parenteral administration must be ensured. The storage container must therefore be designed so that it can be sterilized, when filled, using the conventional processes, or, after sterilization of the individual parts, it can be assembled, filled with sterile medicament suspension and sealed, all under aseptic conditions.

It is known that lubricant dispersions and paints which are filled into spray cans contain steel balls as mixing elements. However, the lubricants are easily dispersible substances, such as molybdenum sulfide and graphite, which can easily be converted into a sprayable form by a few shaking movements. In contrast, a relatively viscous system is present in the case of paints, meaning that high shear forces, which simplify redispersal, are produced on shaking. In addition, these systems contain large amounts of propellent gas, meaning that this type of mixing cannot easily be applied to medicament suspensions. In addition, metal abrasion occurs caused by the friction of the steel balls on the wall of the container, but this does not interfere in the case of these industrial systems. The danger of recrystallization and thus particle enlargement does not exist either, since the dispersed lubricants or pigment particles are completely or virtually insoluble in the administration medium.

Due to the lack of a gas space and—particularly in the case of cylindrical ampules—due to the unfavorable ratio of diameter to length, which, in addition, changes constantly during use when the piston is advanced, it was not to be expected that simple mixing elements, as are known from spray cans, could also be suitable for homogenization in medicament suspensions which are filled into conventional medicament containers without gas bubbles.

In addition, it is known that many medicament crystals—particularly insulin—are sensitive to mechanical load. If, for example, an insulin crystal suspension is stirred in a beaker on a conventional magnetic stirrer, a noticeable proportion of the insulin crystals are triturated due to the action of the magnetic follower. The increase in the surface of the particles which is connected with this causes their dissolution rate, and thus the depot effect, to be altered in an undesired fashion. Such an alteration of the particle size was also feared in the use of mixing elements in medicament containers.

Surprisingly, it has now been found that even medicament suspensions, above all those which are filled so as to be free of gas bubbles, can easily be converted into a homogeneous suspension with the aid of mixing elements if the mixing element is inert, has a suitable size, and has a density which is sufficiently different to that of the medicament suspension. All the parameters mentioned are easily determined here by simple preliminary experiments. A sufficiently different density is taken as being when the density of the mixing element is at least 10%, preferably at least 50%, particularly at least 100%, greater than that of the suspended medicament.

Surprisingly, the particle size of insulin crystal suspensions, as are used in the example shown below, are virtually unaltered under the conditions described.

Since the medicament containers, above all injection ampules, for example conventional cylindrical ampules or twin-chamber syringes (for example Pharm. Ind. 46 (1984, No. 3) 317), are usually made of glass, the mixing elements are advantageously likewise manufactured from glass. However, plastics, for example polymers of fluorinated ethylenes, such as PTFE, or ceramic or metallic, optionally coated elements are also suitable.

The shape of the mixing element can be optimized by appropriate preliminary experiments, care being taken, expediently, that the volume of the mixing element remains small compared to the reservoir, so that comparatively small dead spaces are produced. In general, simple shapes are suitable for the mixing elements, such as cylinders, or, preferably, spheres, but molded articles having a turbulence-generating surface shape, such as spheres with holes, or other complicated shapes are also possible.

"Inert" is taken to mean a mixing element which interacts neither chemically nor physically in an interfering manner with the medicament preparation. Thus, neither a chemical change nor a physical impairment, such as adsorption or abrasion, may occur to a significant extent.

In the context of the invention, a system which permits homogenization by shaking using few tilting or shaking movements is thus suitable.

The invention is described in greater detail in the following examples.

BRIEF DESCRIPTION OF THE DRAWINGS

The accompanying drawing, which is incorporated in and constitutes a part of the specification, illustrates a presently preferred embodiment of the invention and, together with the general description given above and the detailed description of the preferred embodiment given below, serve to explain the principles of the invention. Of the drawings:

FIG. 1 is a side view of a cylindrical ampule incorporating a preferred embodiment of the present invention.

DESCRIPTION OF THE PREFERRED EMBODIMENT

In all examples and comparison examples, the cylindrical ampules (1), represented schematically in FIG. 1, are employed which have, at the top, a movable piston (2) on which may be connected to a piston rod (not represented). The ampule is filled with the medicament suspension (3) so as to be bubble-free and contains one or more mixing elements (4). In the figure, a sphere is represented as mixing element 4 although the invention is not limited to a spherical mixing element. The outlet piece (5) is sealed in a known fashion.

An aqueous depot insulin preparation (Basal H Insulin U-100 Hoechst ®) which contains 0.1 I.U. per μl of insulin is used as medicament suspension. The ease of shaking up the sediment was assessed visually, after a standing time of 12 hours (inverted), by means of tilting movements of 180°.

In comparison examples 1 to 3 and examples 1 to 4, the cylindrical ampules (1) had a length of 62.3 mm and an internal diameter of 6.85 mm.

COMPARISON EXAMPLE 1

No addition of glass beads.
Assessment: Homogenization by shaking up by means of simple tilting movements not possible in an acceptable period of time.

COMPARISON EXAMPLE 2

Addition of one glass bead of diameter 3 mm.
Assessment: Ease of shaking-up not reproduceable. Sediment got into the outlet part of the cylindrical ampule along with a sphere and wedged the sphere there.

COMPARISON EXAMPLE 3

Addition of two glass beads, diameter 3 mm.
Assessment: As in comparison example 2.

EXAMPLE 1

Addition of one glass bead of diameter 4 mm.
Assessment: Homogenization by shaking by means of 6 to 9 tilting movements.

EXAMPLE 2

Addition of two class beads, diameter 4 mm.
Assessment: As in example 1.

EXAMPLE 3

Addition of one glass bead of diameter 5 mm.
Assessment: Homogenization by shaking by means of 3 to 4 tilting movements.

EXAMPLE 4

Addition of one glass bead of diameter 6 mm.
Assessment: As in example 3.

EXAMPLES 5 AND 6

Cylindrical ampules, of length 58 mm and internal diameter 6.85 mm, which contained one glass sphere (diameter 5 mm) were filled with the insulin suspension so as to be free of gas bubbles and were employed in a commercially available insulin "pen".

After different standing times between withdrawals, the contents were resuspended by means of five 180° tilting movements, and 40 μl, corresponding to 4 I.U. of insulin, were dispensed into each of five sample tubes. The insulin content of the individual samples was determined analytically in order to ascertain the homogeneity.

The mean value ($\bar{x}$) of five samples in each case and the relative standard deviation ($s$rel) are collated in the following table from two parallel experimental series with two insulin "pens":

| Standing time before resuspending | $\bar{x}$ (I.U.) | | $s$rel (%) | |
|---|---|---|---|---|
| | Example 5 | Example 6 | Example 5 | Example 6 |
| 6 hours | 4.4 | 3.9 | 11.1 | 5.6 |
| 72 hours | 4.1 | 4.0 | 8.4 | 1.2 |
| 6 hours | 3.9 | 4.0 | 2.3 | 3.3 |
| 16 hours | 3.7 | 4.0 | 4.9 | 5.7 |

We claim:

1. A device for the administration of medicament suspensions comprising: a container for receiving an essentially gas-bubble-free medicament suspension; at least one mixing element disposed in said container, said mixing element being inert towards the suspension and having a density which is greater than the density of the suspension, said at least one mixing element being dimensioned relative to the size of said container such that the suspension is homogenized by shaking movements of said container.

2. The device as claimed in claim 1, comprising a cylindrical container which is sealed at the top by a movable piston and at the bottom by an outlet piece.

3. The device as claimed in claim 1, wherein said mixing element is spherical.

4. The device as claimed in claim 2, having at least three spherical mixing elements.

5. The device as claimed in claim 1, wherein the density of the mixing element is at least 10% greater than that of the suspension.

6. The device as claimed in claim 1, wherein the density of the mixing element is at least 50% greater than that of the suspension.

7. The device as claimed in claim 1, wherein the density of the mixing element is at least 100% greater than that of the suspension.

8. The device as claimed in claim 1, wherein the mixing element is formed of glass, metal, plastic or ceramic.

9. The device as claimed in claim 8, wherein the mixing element is coated with a substance inert toward said suspension.

10. The device as claimed in claim 1, wherein said suspension is a crystal suspension.

11. The device as claimed in claim 1, wherein said suspension is an insulin crystal suspension.

* * * * *

UNITED STATES PATENT AND TRADEMARK OFFICE
CERTIFICATE OF CORRECTION

PATENT NO. : 4,850,966

DATED : July 25, 1989

INVENTOR(S) : Ulrich Grau et al

It is certified that error appears in the above-identified patent and that said Letters Patent is hereby corrected as shown below:

Claim 1, column 4, line 53, change "for receiving" to --filled with--.

Signed and Sealed this

Thirteenth Day of November, 1990

Attest:

HARRY F. MANBECK, JR.

*Attesting Officer*  *Commissioner of Patents and Trademarks*

REEXAMINATION CERTIFICATE (2377th)
United States Patent [19]
Grau et al.

[11] B1 4,850,966
[45] Certificate Issued  Sep. 6, 1994

[54] DEVICE FOR THE ADMINISTRATION OF MEDICAMENT SUSPENSIONS

[75] Inventors: Ulrich Grau; Wolfgang Pohler, both of Hofheim am Taunus, Fed. Rep. of Germany

[73] Assignee: Hoechst Aktiengesellschaft, Fed. Rep. of Germany

Reexamination Request:
No. 90/003,082, Jun. 3, 1993

Reexamination Certificate for:
Patent No.: 4,850,966
Issued: Jul. 25, 1989
Appl. No.: 17,617
Filed: Feb. 24, 1987

Certificate of Correction issued Jul. 25, 1989.

[30]  Foreign Application Priority Data

Feb. 26, 1986 [DE] Fed. Rep. of Germany ....... 3606163

[51] Int. Cl.$^5$ .............................................. A61M 37/00
[52] U.S. Cl. ...................... 604/82; 604/903
[58] Field of Search ................. 604/82, 187, 218, 232, 604/903

[56] References Cited

U.S. PATENT DOCUMENTS

3,390,492  1/1976  Hatsuno et al. .
3,729,003  4/1973  Hurschman .

FOREIGN PATENT DOCUMENTS

505575  8/1930  Fed. Rep. of Germany .

OTHER PUBLICATIONS

*Balance,* Apr. 1983, pp. 11, 19.
*The Lancet,* Jan. 1981, pp. 189, 190.
SCRIP, No. 1034, Sep. 16th, 1985.
APPI Data Sheet Compendium 1986–87 (Oct. 1986).
ABPI Data Sheet Compendium 1985–86 (Jul. 1985).
NOVO Insulin Product Brochure (undated).
NOVO Insulin Product Brochure HN-08-85-13 (Sep. 1985).

*Primary Examiner*—John D. Yasko

[57]  ABSTRACT

A medicament container, such as an injection ampule, for multiple administration of medicament suspensions for containers is filled with medicament so as to be free of gas bubbles, and includes at least one inert mixing element of suitable size whose density is different from that of the suspension. The mixing element acts to homogenize the medicament suspension as the container is shaken.

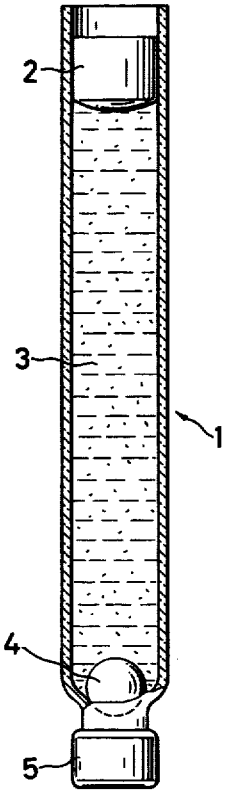

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1-11 is confirmed.

* * * * *